US006150312A

United States Patent [19]

Puvvada et al.

[11] Patent Number: 6,150,312

[45] **Date of Patent: *Nov. 21, 2000**

[54] LIQUID COMPOSITION WITH ENHANCED LOW TEMPERATURE STABILITY COMPRISING SODIUM TRICEDETH SULFATE

[75] Inventors: Sudhakar Puvvada, Rutherford; Shuman Mitra, Cliffside Park, both of N.J.

[73] Assignee: Unilever Home & Personal Care USA, a division of Conopco, Inc., Greenwich, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/286,042

[22] Filed: Apr. 5, 1999

[51] Int. Cl.[7] .............................. C11D 17/00; A61K 7/50; A61K 7/48

[52] U.S. Cl. .......................... 510/130; 510/158; 510/159; 510/417; 510/424; 510/490; 510/491

[58] Field of Search ..................................... 510/156, 424, 510/426, 499, 123, 125, 130, 158, 159, 417, 490, 491

[56] References Cited

U.S. PATENT DOCUMENTS

| | | | |
|---|---|---|---|
| 5,543,074 | 8/1996 | Hague et al. | 510/122 |
| 5,612,307 | 3/1997 | Chambers et al. | 510/406 |

FOREIGN PATENT DOCUMENTS

| | | |
|---|---|---|
| 97/05857 | 2/1997 | WIPO . |

OTHER PUBLICATIONS

U.S. Ser. No. 08/993,497 to Villa, filed Dec. 18, 1997, discussed on p. 4, last paragraph of the application.

*Primary Examiner*—Necholus Ogden
*Attorney, Agent, or Firm*—Ronald A. Koatz

[57] ABSTRACT

The invention relates to liquid cleansing compositions in lamellar phase. Use of specific anionic surfactant has been found to enhance both initial viscosity and freeze thaw (low temperature) viscosity/stability.

11 Claims, No Drawings

LIQUID COMPOSITION WITH ENHANCED LOW TEMPERATURE STABILITY COMPRISING SODIUM TRICEDETH SULFATE

BACKGROUND

1. Field of the Invention

The present invention relates to liquid cleansing compositions of the type typically used in skin cleansing or shower gel compositions which compositions are "structured" lamellar phase compositions. Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

2. Background of the Invention

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps * suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning).

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. Again, however, they are generally more expensive to make (e.g., they are restricted as to which surfactants can be used and often require greater concentration of surfactants).

In general, lamellar phase compositions are easy to identify by their characteristic focal conic shape and oily streak texture while hexagonel phase exhibits angular fan-like texture. In contrast, micellar phases are optically isotropic.

It should be understood that lamellar phases may be formed in a wide variety of surfactant systems using a wide variety of lamellar phase "inducers" as described, for example, in applicants publication, WO 97/05857. Generally, the transition from micelle to lamellar phase are functions of effective average area of headgroup of the surfactant, the length of the extended tail, and the volume of tail. Using branched surfactants or surfactants with smaller headgroups or bulky tails are all effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring lamellar dispersions is using freeze fracture electron microscopy. Micrographs generally will show lamellar microstructure and close packed organization of the lamellar droplets (generally in size range of about 2 microns).

One problem with certain lamellar phase compositions is that they tend to lose their lamellar stability in colder temperatures (e.g., 0 to 45° F.). While not wishing to be bound by theory, this may be because, in cold conditions, the oil droplets become less flexible and the spherical structure characterizing the lamellar interaction breaks into lamellar sheets instead.

In applicants' U.S. Ser. No. 08/993,497 to Villla, it was found that use of certain polymeric emulsifiers (e.g., dipolyhydroxystearate) helped enhance low temperature viscosity.

BRIEF DESCRIPTION OF THE INVENTION

Unexpectedly, applicants have found specific anionic surfactants, e.g., branched $C_{10}$–$C_{22}$, preferably branched $C_{10}$–$C_{16}$ alkyl, alkali metal ether sulfates (i.e., having at least one branch from the alkyl portion of the alkyl ether sulfate), provide enhanced freeze thaw stability in structured liquid compositions relative to compositions not comprising the branched $C_{10}$–$C_{22}$ alkyl, alkali metal ether sulfate. The alkyl ether sulfate may be used as sole anionic surfactant or in a mixture of anionics wherein the branched ether sulfate comprises about 50% to 100%, preferably 51% to 100% of the anionic surfactant.

More specifically, the invention comprises a liquid cleansing composition, wherein the liquid is in a lamellar phase, comprising:

(a) 5% to 50% by wt. of a surfactant system comprising:
  - (i) 0.5 to 25%, preferably 1 to 15% by wt. total composition of one or more anionic surfactant, where the one anionic or at least one of the more than one anionic comprises branched $C_{10}$–$C_{22}$ alkyl, alkali metal, ether sulfate (where mixture is used, branched ether sulfate comprises at least about 50% of anionic mixture);
  - (ii) preferably an amphoteric and/or zwitterionic surfactant (e.g., betaine or alkali metal $C_8$–$C_{20}$ amphoacetate) or mixtures thereof (e.g., amphoteric/zwitterionic or mixture of amphoteric/zwitterionic comprises 0 to 25% by wt., preferably 0.1 to 20% by wt.); and (b) 1 to 15% by wt., preferably 2% to 10% by wt. of a fatty acid or ester thereof (e.g., straight chained fatty acid such as lauric acid or branched fatty acid such as isostearic acid);

wherein said compositions have initial viscosity of greater than 20,000 to 300,000 centipoises (cps) measured at 0.5 RPM using T-bar spindle A, preferably 40,000 cps to 250,000 cps, more preferably from about 50,000 to about 200,000 cps, and freeze thaw viscosity (measured after at least one cycle, preferably at least 2 cycles, most preferably at 3 cycles of 0° F. to room temperature freeze thaw cycles) defined either by having viscosity greater than about 30,000 cps, preferably greater than 35,000 (again measured at 0.5 RPM using T-bar spindle A) or by having a percent drop in viscosity relative to initial viscosity of no more than 40%.

Ideally, there should be no change in viscosity from initial viscosity although this of course is not always possible. The invention may also be defined in this regard, as noted, in that the drop in viscosity after freeze/thaw should be 40% or less, preferably 35% or less than the initial viscosity.

DETAILED DESCRIPTION OF THE INVENTION

The present invention relates to liquid lamellar cleansing compositions, particularly liquid cleansing compositions comprising:

(a) 5% to 50% by wt. of a surfactant system comprising one or more anionic surfactants wherein at least branched $C_{10}$–$C_{22}$, preferably $C_{10}$–$C_{16}$ alkyl, alkali metal ether sulfate must be present as the anionic or within the mixture of anionics and preferably further comprising an amphoteric and/or zwitterionic surfactant or mixtures thereof; and (b) 1 % to 15% by wt., preferably 2 to 10% by wt. of a fatty acid or ester thereof (as lamellar phase inducing structurant)

wherein said compositions have initial viscosity of greater than 20,000 to 300,000 cps measured at 0.5 RPM using T-bar spindle A, preferably 40,000 cps to 250,000 cps, more preferably from about 50,000 to about 200,000 cps, and freeze thaw viscosity (measured after at least one cycle, preferably at least 2 cycles, most preferably at 3 cycles of 0° F. to room temperature freeze thaw cycles) defined either by having a viscosity greater than about 30,000 cps, preferably greater than 35,000 (again measured at 0.5 RPM using T-bar spindle A) or by having a percent drop in viscosity relative to initial viscosity of no more than 40%.

Surfactants

The surfactant system of the subject invention comprises 5 to 50% by weight, preferably 10 to 40% by wt. of the composition and comprises:

(a) one or more anionic surfactants wherein the one, if only one is used, or at least one of the anionics, if a mixture is used, must be branched $C_{10}$–$C_{22}$, preferably $C_{10}$–$C_{16}$ alkyl, alkali metal ether sulfate;

(b) amphoteric and/or zwitterionic surfactant; and (c) optional nonionic surfactant As noted, the anionic surfactant itself (or among the mixture of anionic surfactants must be found) is branched $C_{10}$–$C_{22}$ alkyl, alkali metal ether sulfate. A preferred ether sulfate is branched $C_{13}$ (trideceth) sulfate, particularly branched sodium tridecyl ether sulfate. Branching may occur at one or two or more locations in the alkali backbone.

If used alone, the ether sulfate generally comprises 1 to 25% by wt. of the total composition and, if used as one of 2 or more anionics, it will generally comprise 1 to 12.5% by wt. of the total composition.

If not used alone, additional anionic surfactant (which may comprise 0.5% to 12.5% by wt. of total composition) may be used is follows:

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium laurel ether sulfates are preferred.

These differ from ether sulfates of the invention in that they are not branched.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$R^4O_2CCH_2CH(SO_3M)CO_2M$;

amido-MEA sulfosuccinates of the formula $R^4CONHCH_2CH_2O_2CCH_2CH(SO_3M)CO_2M$ wherein $R^4$ ranges from $C_8$–$C_{22}$ alkyl and M is a solubilizing cation;

amido-MIPA sulfosuccinates of formula $RCONH(CH_2)CH(CH_3)(SO_3M)CO_2M$ where M is as defined above.

Also included are the alkoxylated citrate sulfosuccinates; and alkoxylated sulfosuccinates such as the following:

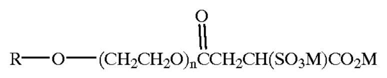

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$R—(CH_2CH_2O)_nCO_2M$ wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

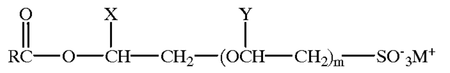

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the "additional" anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

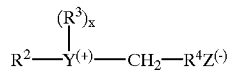

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N ,N-di(2-hydroxyethyl)-N-octadecylammonio]-butane-1-carboxylate;

5-[S-3-hydroxypropyl—S—hexadecylsulfonio]-3-hydroxypentane-1-sulfate;

3-[P, P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1-carboxylate;

3-[S-ethyl—S—(3-dodecoxy-2-hydroxypropyl)sulfonio]-propane-1-phosphate;

3-[P,P-dimethyl-P-dodecylphosphonio]-propane-1-phosphonate; and

5-[N, N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

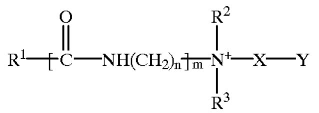

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

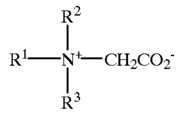

and amido betaines of formula:

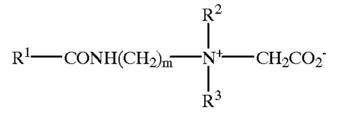

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

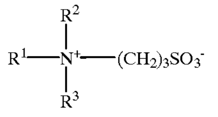

or

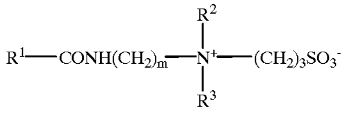

where m is 2 or 3, or variants of these in which —$(CH_2)_3SO^-_3$ is replaced by

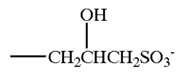

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, preferably 5% to 15% of the composition.

A preferred surfactant system of the invention comprises unbranched alkyl ether sulfate together with branched alkyl ether sulfates of the invention, optionally further in combination with betaine and/or amphoacetate.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

Structurant

The compositions of the invention utilize about 1% to 15% by wt., preferably 2 to 10% by wt. of a structuring agent which works in the compositions to form a lamellar phase. Such lamellar phase enables the compositions to suspend particles more readily (e.g., emollient particles) while still maintaining good shear thinning properties. The lamellar phase also provides consumers with desired rheology ("heaping").

The structurant is a fatty acid or ester derivative thereof.

Examples of fatty acids which may be used are $C_{10}$–$C_{22}$ acid (e.g. lauric, oleic etc.), isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Oil/Emollient

One of the principle benefits of the invention is the ability to suspend oil/emollient particles in a lamellar phase composition. The following oil/emollients may optionally be suspended in the compositions of the invention.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: acetylated lanolin alcohols, lanolin, lard, mink oil and tallow.

Other examples of oil/emollients include mineral oil, petrolatum, silicone oil such as dimethyl polysiloxane, lauryl and myristyl lactate.

The emollient/oil is generally used in an amount from about 1 to 20%, preferably 1 to 15% by wt. of the composition. Generally, it should comprise no more than 20% of the composition.

In addition, the compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330-Polyquaternium 39; and Jaguar® type conditioners.

Another optional ingredient which may be added are the deflocculating polymers such as are taught in U.S. Pat. No. 5,147,576 to Montague, hereby incorporated by reference.

Other ingredients which may be included are exfoliants such as polyoxyethylene beads, walnut sheets and apricot seeds The compositions of the invention, as noted, are lamellar compositions. In particular, the lamellar phase comprises 30 to 80%, preferably 40 to 70% of the total phase volume. The phase volume may be measured, for example, by conductivity measurements or other measurements which are well known to those skilled in the art. While not wishing to be bound by theory, higher phase volume is believed to provide better suspension of emollients.

The invention will now be described in greater detail by way of the following non-limiting examples. The examples are for illustrative purposes only and not intended to limit the invention in any way.

Except in the operating and comparative examples, or where otherwise explicitly indicated, all number in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLES

Tests in lamellar structured shower gel compositions where conducted in the following base compositions:

| Base | |
|---|---|
| Ingredient | % by Wt. |
| Sodium Trideceth Sulfate | 15% |
| Sodium Lauryl Ether Sulfate (SLES) | 0–10% |
| Amphoteric Surfactant (e.g., Sodium Lauroamphoacetate) | 5–15% |
| Oil/Emollient (e.g., Sunflower Seed Oil; Silicone; Petrolatum) | 0–15% |
| Opacifier/Colorant | 0–2% |
| Perfume/Preservative | 0–3% |
| Lamellar Inducing Fatty Acid (e.g., Isostearic Acid) | 1–8% |

Viscosity measurements were made in accordance with the following protocol:

Viscosity Measurement

Scope:

This method covers the measurement of the viscosity of the finished product. It is used to measure the degree of structuring of the product.

Apparatus:

Brookfield RVT Viscometer with Helipath Accessory;

Chuck, weight and closer assembly for T-bar attachment;

T-bar Spindle A;

Plastic cups diameter greater than 2.5 inches.

Procedure:

1. Verify that the viscometer and the helipath stand are level by referring to the bubble levels on the back of the instrument.
2. connect the chuck/closer/weight assembly to the Viscometer (Note the left-hand coupling threads).
3. Clean Spindle A with deionized water and pat dry with a Kimwipe sheet. Slide the spindle in the closer and tighten.
4. Set the rotational speed at 0.5 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C.
6. Lower the spindle into the product (~¼ inches). Set the adjustable stops of the helipath stand so that the spindle does not touch the bottom of the plastic cup or come out of the sample.
7. Start the viscometer and allow the dial to make one or two revolutions before turning on the Helipath stand. Note the dial reading as the helipath stand passes the middle of its downward traverse.
8. Multiply the dial reading by a factor of 4,000 and report the viscosity reading in cps.

Examples 1–3

The following table clearly shows the effect of sodium trideceth sulfate (STDS) in enhancing F/T stability of a structured liquid formulation:

| Example | 1 | 2 | 3 |
|---|---|---|---|
| Sodium tricedeth sulfate | 10 | 0 | 10 |
| Sodium lauryl ether sulfate | 0 | 10 | 0 |
| Cocoamidopropyl betaine | 0 | 0 | 0 |
| Sodium lauro amphoacetate | 15 | 15 | 15 |
| Sunflower oil | 0 | 0 | 0 |
| Lauric acid | 3.2 | 3.2 | 0 |
| Isostearic acid | 0 | 0 | 6 |
| Citric acid | 1.7 | 1.7 | 1.7 |
| R/T viscosity (T-bar), cps | 57600 | 64000 | 236800 |
| F/T viscosity (T-bar), cps | 38400 | 9600 | 227200 |
| % drop | 33 | 85 | 4 |

Comparing Examples 1 and 2, we find a 33% drop in viscosity in the formulations with STDS versus an 85% drop in viscosity in the formulations without STDS. Formulation 3 which also uses STDS with a soluble structurant (isostearic acid) undergoes a minimal (4%) decrease in viscosity under F/T conditions.

Examples 4–5 (Lower Surfactant Level)

| Example | 4 | 5 |
|---|---|---|
| Sodium tricedeth sulfate | 6 | 0 |
| Sodium lauryl ether sulfate | 0 | 6 |
| Cocoamidopropyl betaine | 0 | 0 |
| Sodium lauro amphoacetate | 9 | 9 |
| Sunflower oil | 15 | 15 |
| Lauric acid | 3.2 | 3.2 |
| Isostearic acid | 0 | 0 |
| Citric acid | 1.7 | 1.7 |
| R/T viscosity (T-bar), cps | 294400 | 48000 |
| F/T viscosity (T-bar), cps | 291200 | 19200 |
| % drop | 1 | 60 |

Similar trends to those of Examples 1–3 are found in formulations with and without STDS when the total actives are reduced to 15% (compared to 25% active in Examples 1–3). In this case, the differences in F/T viscosities are more dramatic (Examples 4 and 5). For example, Example 4 using STDS undergoes a mere 1% decrease in viscosity whereas Example 5, which doesn't contain STDS, undergoes a 60% decrease in F/T viscosity.

Examples 6–8 (Use of Different Amphoterics)

| Example | 6 | 7 | 8 |
|---|---|---|---|
| Sodium tricedeth sulfate | 10 | 0 | 10 |
| Sodium lauryl ether sulfate | 0 | 10 | 0 |
| Cocoamidopropyl betaine | 15 | 15 | 15 |
| Sodium lauro amphoacetate | 0 | 0 | 0 |
| Sunflower oil | 0 | 0 | 0 |
| Lauric acid | 3.2 | 3.52 | 0 |
| Isostearic acid | 0 | 0 | 5 |
| Citric acid | 1.7 | 1.7 | 1.7 |
| R/T viscosity (T-bar), cps | 25600 | 22400 | 64000 |
| F/T viscosity (T-bar), cps | 16000 | 6400 | 51200 |
| % drop | 38 | 72 | 20 |

When betaine was used as the amphoteric surfactant, formulations prepared with STDS also exhibited improved F/T stability. For example, the viscosity drop in Examples 6 (with STDS) and 7 (without STDS) were 38% and 72% respectively. Example 8 (similar to Sample 6) using isostearic acid undergoes a 20% drop in viscosity under F/T conditions.

Examples 9–10 (Lower Surfactant; Betaine)

| Example | 9 | 10 |
|---|---|---|
| Sodium tricedeth sulfate | 6 | 0 |
| Sodium lauryl ether sulfate | 0 | 6 |
| Cocoamidopropyl betaine | 9 | 9 |
| Sodium lauro amphoacetate | 0 | 0 |
| Sunflower oil | 10 | 10 |
| Lauric acid | 3.6 | 3.6 |
| Isostearic acid | 0 | 0 |
| Citric acid | 1.4 | 1.4 |
| R/T viscosity (T-bar), cps | 67200 | 60800 |
| F/T viscosity (T-bar), cps | 48000 | 16000 |
| % drop | 29 | 74 |

The differences in viscosity drop with and without STDS (Examples 9 and 10 respectively) were even more dramatic when the total surfactant levels were reduced to 15%. The amphoteric surfactant was betaine. Example 9 (using STDS) went through a 29% viscosity decrease while the viscosity of Example 10 (without STDS) decreased by 74%.

Examples 11–12 (Anionic Mixtures)

| Example | 11 | 12 |
|---|---|---|
| Sodium tricedeth sulfate | 4.5 | 4.5 |
| Sodium lauryl ether sulfate | 4.5 | 4.5 |
| Cocoamidopropyl betaine | 0 | 0 |
| Sodium lauro amphoacetate | 13.5 | 13.5 |
| Sunflower oil | 5 | 5 |
| Lauric acid | 3 | 3.2 |
| Isostearic acid | 0 | 0 |
| Glycerine | 2 | 2 |
| Citric acid | 1.9 | 1.6 |
| Fragrance | 1 | 1 |
| Guar hydroxypropyl trimonium chloride | 0.5 | 0.5 |
| DMDM Hydantoin | 0.2 | 0.2 |
| EDTA | 0.02 | 0.02 |
| EHDP | 0.02 | 0.02 |
| R/T viscosity (T-bar), cps | 154000 | 134000 |
| F/T viscosity (T-bar), cps | 151000 | 126000 |
| % drop | 2 | 6 |

Formulations 11 and 12, were prepared with a 1:1 (active) combination of STDS and SLES as the anionic surfactants, differing in the levels of lamellar structurants. The F/T viscosity drop for both these formulations is between 2–6%.

We claim:

1. A liquid lamellar cleansing composition comprising:

(a) 5% to 50% by wt. of a surfactant system comprising:

(i) one or more anionic surfactants where the one anionic or one of the at least two anionics is a sodium tricedeth sulfate;

(ii) 0.1 to 25% by wt. total composition of an additional surfactant selected from the group consisting of amphoteric, zwitterionic or mixtures thereof; and (b) 1 % to 15% by wt. fatty acid or ester thereof;

wherein composition has initial viscosity of 20,000 to 300,000 cps. measured at 0.5 RPM using T-bar spindle A; and freeze-thaw viscosity defined either by having viscosity greater than about 30,000 cps also measured at 0.5 RPM using T-bar spindle A; or by having a percent drop of viscosity relative to initial viscosity of no more than about 40%.

2. A composition according to claim 1, wherein if more than one anionic is used, additional anionic is acyl isethionate.

3. A composition according to claim 1, comprising 0.1 to 25% by wt. composition anionic surfactant or surfactants.

4. A composition according to claim 1, wherein amphoteric surfactant is betaine.

5. A composition according to claim 1, wherein amphoteric surfactant is lauro amphoacetate.

6. A composition according to claim 1, wherein the fatty acid is isostearic acid.

7. A composition according to claim 1, comprising 2% to 10% by wt. fatty acid.

8. A composition according to claim 1, wherein initial viscosity is 40,000 to 250,000 cps.

9. A composition according to claim 1, wherein initial viscosity is 50,000 to 200,000 cps.

10. A composition according to claim 1, wherein percentage drop in viscosity between initial and final viscosity is 35% or less.

11. A composition according to claim 1, wherein lamellar phase volume is 30 to 80% of total phase volume.

* * * * *